United States Patent [19]
Furcht et al.

[11] Patent Number: 5,294,551
[45] Date of Patent: Mar. 15, 1994

[54] CELL CULTURE SUBSTRATE COATED WITH POLYPEPTIDES HAVING FIBRONECTIN ACTIVITY

[75] Inventors: Leo T. Furcht; James B. McCarthy, both of Minneapolis, Minn.

[73] Assignee: Regents of the University of Minnesota, Minneapolis, Minn.

[21] Appl. No.: 942,597

[22] Filed: Sep. 9, 1992

Related U.S. Application Data

[60] Division of Ser. No. 662,360, Feb. 28, 1991, Pat. No. 5,171,360, which is a division of Ser. No. 225,045, Jul. 27, 1988, Pat. No. 5,019,646, which is a continuation-in-part of Ser. No. 89,073, Aug. 25, 1987, Pat. No. 4,839,464.

[51] Int. Cl.$^5$ ............... C12N 5/00; C12N 11/08; C12N 11/06; C07K 7/00
[52] U.S. Cl. ............... 435/240.243; 435/174; 435/180; 435/181; 435/240.23; 435/240.24; 530/326; 530/328; 530/329; 530/815; 623/11
[58] Field of Search ............... 530/328, 326, 329, 815; 435/240.23, 240.24, 240.243, 174, 180, 181; 623/11

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 5,147,797 | 9/1992 | McCarthy et al. | 435/240.243 |
| 5,171,271 | 12/1992 | Furcht et al. | 423/11 |

*Primary Examiner*—David M. Naff
*Attorney, Agent, or Firm*—Merchant, Gould, Smith, Edell, Welter & Schmidt

[57] ABSTRACT

A composition which can bind heparin and promote cellular adhesion and neurite outgrowth is provided which consists essentially of a polypeptide of the formula:

tyr-glu-lys-pro-gly-ser-pro-pro-arg-glu-val-val-pro-arg-pro-arg-pro-gly-val, lys-asn-asn-gln-lys-ser-glu-pro-leu-ile-gly-arg-lys-lys-thr-asp-glu-leu, lys-asn-asn-gln-lys-ser-glu-pro-leu-ile-gly-arg-lys-lys-thr, leu-ile-gly-arg-lys-lys-thr, tyr-arg-val-arg-val-thr-pro-lys-glu-lys-thr-gly-pro-met-lys-glu, ser-pro-pro-arg-arg-ala-arg-val-thr, trp-gln-pro-pro-arg-ala-arg-ile, or mixtures thereof. Medical devices such as prosthetic implants, percutaneous devices and cell culture substrates coated with the polypeptide composition are also provided. Cell culture substrates provided can be made of a synthetic resin and in the form of a bead, microporous fiber or well of a microtiter plate.

5 Claims, 6 Drawing Sheets

Relative Heparin Binding of Peptides IIa, CSI

Localization of Heparin Binding Activity in Peptide IIa

FIG. 11

1) --------------------TAGPDQTEMTIEGLQPTVEYVSVYAGNPSGESQPLVQTAVT/

2) AIPAPTDLKFTQVTPTSLAQMTPPNVQLIGYRVRVTPKEKTGPMKEINLAPDSSSVVVSGLMVATKIEVSVTALKDTLTSRPAQGVVTTLI

3) NVSPPRRARVTDATETTITISWRTKTETITGFQVDAVPANGQTPIQRTIKPDVRSYTITGLQPGTDYKILYLYTLNDNARSSPVVIDAST

4) AIDAPSMLRPLATTPNSLLVSWQPPRARITGYIIKYEKPGSPPREVVPRPRPGVTEATITGLEPGTEYTIYVIALKNMQKSEPLIGRKKT

5) DELPQLVTLPHPNLHGPEILDVPSTVQKTPFVTHPGYDTGNGIQLPGTSGQQPSVGQQMIFEEHGFRRTTPPTTATPIRERPRPYPPNV(GEEIQIGHIPREDVDYHLTPHGPGLNPNAST)

6) GQEALSQITISWTPF--------

1583 (arrow above AGNPSGESQPLVQTAVT)

2040 (bracket over GEEIQIGHIPREDVDYHLTPHGPGLNPNAST and RERPRPYPPNV)

CELL CULTURE SUBSTRATE COATED WITH POLYPEPTIDES HAVING FIBRONECTIN ACTIVITY

GRANT INFORMATION

The present invention was made with the support of Grant No. CA21463 from the National Institutes of Health. The Government has certain rights in the invention.

This is a division of application Ser. No. 07/662,360, filed Feb. 28, 1991, now U.S. Pat. No. 5,171,360, which is in turn a divisional of application Ser. No. 07/225,045, filed Jul. 27, 1988, now U.S. Pat. No. 5,019,646, which is in turn a continuation-in-part of application Ser. No. 89,073, filed Aug. 25, 1987, now U.S. Pat. No. 4,839,464.

BACKGROUND OF THE INVENTION

The adhesion of mammalian cells to the extracellular matrix is of fundamental importance in regulating growth, adhesion, motility and the development of proper cellular phenotype. This has implications for normal development, wound healing, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagens, proteoglycans and noncollagenous glycoproteins. The extracellular matrix molecule which has been most intensively studied with regard to cell adhesion is the noncollagenous cell adhesion glycoprotein, fibronectin, which is present in plasma, cell matrices, basal lamina and on cell surfaces. The plasma form of fibronectin consists of a disulfide-bonded dimer having a molecular weight of 450,000 daltons. The two subunit chains ("A" and "B"), each of about 220,000 daltons, are observed under reducing conditions. This form of fibronectin will be referred to as "fibronectin" hereinafter.

Fibronectin, as with other components of the extracellular matrix, has the ability to bind to itself, to other matrix constituents, and to the surface of cells, via discrete domains an the molecule. For example, fibronectin promotes the attachment of suspended cells to collagen. (See L. T. Furcht, *Modern Cell Biology*, B. Satir, ed., Alan R. Liss, Inc., N.Y., Vol. I (1983) at pages 53–117). The primary structure of one adhesion sequence within fibronectin was originally deduced by M. D. Pierschbacher et al. using monoclonal antibody data and direct sequence analysis. This sequence was found to be a tetrapeptide consisting of arginyl-glycyl-aspartyl-serine CRGOS) (M. D. Pierschbacher and E. Ruoslahti, *PNAS USA*, 81, 5985 (1984)). Peptides containing the RGDS sequence are capable of directly promoting the adhesion of certain cell types, and high levels of soluble RGDS will partially disrupt cell adhesion to intact fibronectin. Cell adhesion to the RGDS sequence in fibronectin is believed to occur by the interaction of this sequence with a cell surface glycoprotein complex termed "integrin".

Despite the importance of the RGDS/integrin complex in fibronectin medicated cell adhesion, several lines of evidence point to the involvement of additional cellular receptors and different fibronectin determinants in this process. Many cell types form focal adhesions on intact fibronectin. These structures represent regions of close apposition between the plasma membrane and the substratum. These sites also represent insertion points for actin-rich stress fibers, and have been shown to contain several actin-associated cytoskeletal proteins. Focal adhesion sites also contain several classes of cell surface molecules implicated in cell adhesion, including integrin, heparan sulfate, chondroitin sulfate, or other proteoglycans and gangliosides.

The action of multiple receptors for fibronectin has been implicated in adhesion plaque formation. Cells adherent to either RGOS-containing fragments or heparin-blinding, adhesion promoting ligands (e.g., platelet factor 4 or heparin binding fragments of fibronectin) form only close contacts. In contrast, cells adherent on both RGDS-containing fragments and heparin-binding ligands display fully developed focal adhesions. Additionally, antibodies against heparin binding fragments of fibronectin inhibit focal adhesion formation, without drastically inhibiting the level of cell adhesion on intact fibronectin. Collectively, these results support a role of heparin-binding domain(s) of fibronectin in promoting normal and malignant cell adhesion, and in regulating phenotypic expression of cells.

J. B. McCarthy et al., in *J. Cell Biol.*, 102 179 (1986) recently published results identifying a 33 kD carboxyl terminal heparin-binding fragment of fibronectin which promotes the adhesion and spreading of metastatic melanoma cells by an RGDS independent mechanism. This fragment originates from the A chain of the fibronectin molecule. It binds heparan sulfate proteoglycan and also promotes the adhesion of neurons and the extension of neurites by these cells.

Therefore, a need exists to isolate and characterize the subset of peptides within this fragment which are responsible for its wide range of biological activities. Such lower molecular weight oligopeptides would be expected to be more readily obtainable and to exhibit a narrower profile of biological activity than the 33 kD fragment, thus increasing their potential usefulness as therapeutic or diagnostic agents.

BRIEF DESCRIPTION OF THE INVENTION

The present invention provides biologically-active polypeptides which represent fragments of the 33 kD carboxyl terminal, heparin-binding region located on the A chain of fibronectin. Two of these polypeptides, which can be prepared in substantially pure form by conventional solid phase peptide synthesis, have the formulas:

tyr-glu-lys-pro-gly-ser-pro-pro-arg-glu-val-val-pro-arg-pro-arg-pro-gly-val   (I)

and lys-asn-asn-gln-lys-ser-glu-pro-leu-ile-gly-arg-lys-lys-thr-asp-glu-leu   (II)

Polypeptide I formally represents isolated fibronectin residues 1906–1924, while polypeptide II formally represents isolated fibronectin residues 1946–1963. The single letter amino acid codes for these polypeptides are YEKPGSPPREVVPRPRPGV and KNNQKSEPLIGRKKTDEL, respectively.

Peptide I exists in all isoforms of fibronectin. In contrast, the first 15 residues of peptide II exist in all isoforms, whereas the last three residues in peptide II are a part of a region of structural heterogeneity which occurs only in certain isoforms in fibronectin (termed A chains). In the case of plasma fibronectin, this region of structural heterogeneity, termed type III cs, can be up to 89 residues long. The 33 kD heparin-binding fragment arises from A chains and includes part of this type III cs sequence.

Recently, Humphries et al., *J. Biol. Chem.*, 262, 6886-6892 (1987), reported that the type III cs connecting segment of fibronectin has cell adhesion-promoting activity. Humphries et al. constructed overlapping peptides which represented the entire type III cs sequence and tested these peptides for the ability to promote the adhesion and spreading of fibroblasts and melanoma cells. The results of these studies indicated that the first 24 residues of this type III cs connecting sequence promoted melanoma cell adhesion and spreading. The sequence of the biologically active peptide, termed CS I, was asp-glu-leu-pro-gln-leu-val-thr-leu-pro-his-pro-asn-leu-his-gly-pro-glu-ile-leu-asp-val-pro-ser-thr (DELPQLVTLPHPNLHGPEILDVPST), and corresponds to residues 1961-1985. Thus, an overlap exists between the last three residues of peptide II and the first three residues of the CS I peptide reported by Humphries et al. However, the peptide reported by Humphries et al. differs chemically from either peptides I or II. CS I is more hydrophobic, and totally lacks lysine or arginine residues. The significant chemical properties of each peptide are summarized on Table I, below:

TABLE I

| Peptide | Residue Nos. | Hydropathy Index | Net Charge |
|---|---|---|---|
| I | 1906-1924 | -24.3 | +2 |
| II | 1946-1963 | -32.5 | +2 |
| CS I | 1961-1985 | -9.9 | -4 |

The "hydropathy index" is calculated according to the method of Kyte and Doolittle, *J. Mol. Biol.*, 157, 105-132 (1982). According to this method, the more (—) a value is, the more hydrophilic it is. Thus, the CS I peptide is much more hydrophobic than peptides I and II.

The net charge of each peptide is calculated by assigning a (+1) charge to each lysine (K) and arginine (R) residue, and a (—1) charge to each glutamic acid (E) and aspartic acid (D) residue. Additional residues are assumed to be uncharged. These charges would be expected under the conditions of heparin binding and cell adhesion assays, which are performed near neutrality (pH 6.8 to 7.4). The only other residue which could contribute significantly to total charge is histidine (H), which occurs twice in the CS I peptide but would be uncharged under the pH conditions of the assays used.

Despite the difference in chemical properties between CS I and peptide II, experiments were carried out to determine whether or not the biological activity of peptide II was related to the three-residue overlap with peptide CS I (residues #1961-1963, DEL). Thus, a polypeptide was synthesized which contained the first 15 amino acid residues of polypeptide II. The formula of this polypeptide, IIa, is shown below:

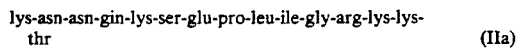

lys-asn-asn-gln-lys-ser-glu-pro-leu-ile-gly-arg-lys-lys-thr                (IIa)

The single letter amino acid code for this polypeptide is KNNQKSEPLIGRKKT, which corresponds to residues 1946-1960. This peptide differs from peptide I in that a.) the total net charge is (+4) and the total hydropathy index is —29.3.

It was found that while IIa bound heparin in a concentration-dependent fashion, peptide CS I failed to bind to heparin at any concentration that was tested. Therefore, the biological activity of each peptide is due to distinct and unique structural determinants.

The present invention is also directed to the biologically active peptide fragments of polypeptides I, II and IIa. For example, the present invention also provides three polypeptides which correspond to the amino terminal third (IIa-A), the central third (IIa-B), and the carboxyl terminal third (IIa-C), sequences of peptide II. Specifically, these peptides have the sequences shown on Table II, below.

TABLE II

| Name | Primary Sequence | Net Charge |
|---|---|---|
| II(amino) (IIa-A) | KNNQKSEP (lys—asn—asn—gln—lys—ser—glu—pro) | +1 |
| II(central) (IIa-B) | KSEPLIGR (lys—ser—glu—pro—leu—ile—gly—arg) | +1 |
| II(carboxyl) (IIa-C) | LIGRKKT (leu—ile—gly—arg—lys—lys—thr) | +3 |

The present invention also provides three additional bioactive polypeptides, which also represent fragments of the 33 kD carboxyl terminal heparin-binding region located on the A chain of fibronectin. These polypeptides, III, IV and V, are structurally distinct from each other and from peptides I and IIa, however, they do share certain chemical properties which are summarized on Table III, below:

TABLE III

| Peptide | Primary Structure | Residue Nos. | Hydropathy Index | Net Charge |
|---|---|---|---|---|
| III | YRVRVTPKEKTGPMKE (tyr—arg—val—arg—val—thr—pro—lys—glu—lys—thr—gly—pro—met—lys—glu) | 1721-1736 | -23.7 | +3 |
| IV | SPPRRARVT (ser—pro—pro—arg—arg—ala—arg—val—thr) | 1784-1792 | -12.2 | +3 |
| V | WQPPRARI (trp—gln—pro—pro—arg—ala—arg—ile) | 1892-1899 | -10.8 | +2 |

Each peptide has an identical net charge, although each peptide derives its charge from different basic residues. Peptide III contains two arginine (R) residues and three lysine (K) residues. Peptides IV and V contain only arginine residues. Furthermore, the charges are clustered in peptides IV and V, whereas the positive charges in peptide III are more dispersed. The dispersal of charge within peptide III is different from that in the other four heparin-binding peptides identified from this region to date. Peptide III is more hydrophilic than either peptide IV or V, but less hydrophilic than peptides I or II.

These synthetic polypeptides were assayed for bioactivity and found to exhibit at least one of the following properties: they (a) promote neurite extension, (b) promote the adhesion and spreading of endothelial cells (c) promote the adhesion and spreading of melanoma cells, and/or (d) promote the binding of heparin to a synthetic substratum. Therefore, it is believed that these polypeptides may be useful to (a) assist in nerve regeneration, (b) promote wound healing and implant acceptance, (c) promote cellular attachment to culture substrata, (d) inhibit the metastasis of malignant cells, and/or (e) bind excess heparin, a condition which can occur in vivo during heparin therapy. Due to the difference in the spectra of biological activities exhibited by the present polypeptides, mixtures thereof are also within the scope of the invention.

Furthermore, since it is expected that further digestion/hydrolysis of polypeptides I, II, IIa and III-V, in vitro or in vivo, will yield fragments of substantially equivalent bioactivity, such lower molecular weight polypeptides are considered to be within the scope of the present invention.

BRIEF DESCRIPTION OF THE DRAWINGS

FIG. 11 is a schematic representation of the amino acid sequence of the portion of the plasma fibronectin molecule from which these peptides are formally derived.

DETAILED DESCRIPTION OF THE INVENTION

Structure of Fibronectin

Figure 1:
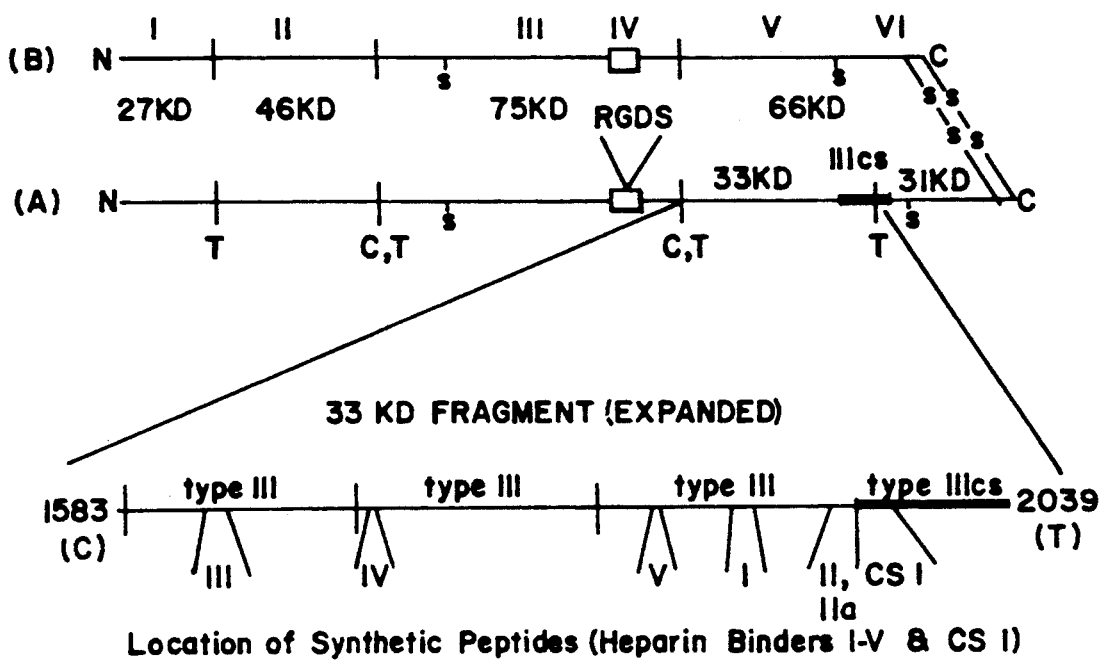
FIG. 1 is a schematic depiction of plasma fibronectin, indicating the relative location of RGDS and CS-I on the protein with respect to the heparin-binding peptides I-V of the present invention, which are located on the 33 kD carboxyl terminal heparin binding fragment of the A chain.

Referring to FIG. 1, the two types of chains (A and B) of plasma fibronectin are shown as a disulfide (-S-S-) bonded heterodimer. The six domains (I-VI) of fibronectin are labeled according to previous nomenclature (L. T. Furcht in *Modern Cell Biology*, B. Satir, ed., Alan R. Liss, Inc., N.Y. (1983) at pages 53-117.) Biological activities within each domain include: (1) weak heparin binding, (II) noncovalent collagen binding, (III) DNA binding, (IV) RGOS-mediated cell adhesion, shown as box (O), (V) heparin binding, RGDS independent cell adhesion, and (VI) free sulfhydryl. The molecular weight estimates of proteolytic fragments containing each domain are based on a previously described digestion and purification scheme. (J. S. McCarthy, *J. Cell Biol.*, 102, 179 (1986)). Proteolytic cleavage sites (X) are shown for trypsin (T) and Cathepsin D (C). By these schemes, domains V and VI isolated from digests of the B chain are located on a 66 kD fragment. In contrast, the A chain digests contain a 33 kD fragment (domain V) and a 31 kD fragment (domain VI). The difference is a result of a trypsin sensitive site in the A-chain specific type IIIcs insert, shown as a bold line.

Amino Terminal Sequence of the Tryptic/Catheotic 66 kD and 33 kD Heparin-Binding Fragments and Carboxyl Terminal Tryptic 31 kD Free-Sulfhydryl Containing Fragment The entire primary structure of fibronectin has either been determined directly (T. E. Peterson et al., *PNAS USA*, 80, 137 (1983)) or has been predicted from recombinant DNA technology. (J. E. Schwarzbauer et al., *Cell*, 135, 421 (1983)). The amino terminal sequences of tryptic/catheptic (t/c) 33 kD, t/c66 kD, and tryptic (t) 31 kD fragments were established by direct amino acid sequencing on an Applied Biosystems gas phase sequenator (Model 470A), in order to determine the exact location of these fragments with respect to the known human sequence.

The first 21 amino acids which were determined for the t/c66 heparin binding fragment (FIG. 11, underlined residues which begin in line 1 and continue in line 2). This fragment starts with the amino acid alanine which corresponds to residue 1583 on intact plasma fibronectin (A. R. Kornblihtt et al., *EMBO J.*, 4, 1755 (1985)). The presence of tyrosine to he amino terminal side of this alanine in intact fibronectin is consistent with a preference of Cathepsin D for peptide bonds involving aromatic residues. The sequence of the t/c66 fragment does not contain the EDIII insert, since the sequence proceeds from a threonine at residue number 1599 (double asterisks followed by a slash at the end of line 1) to an alanine at residue 1690 (first residue, line 2). This lack of the EDIII region is a characteristic feature which distinguishes plasma- or liver-derived fibronectin from cellular, or fibroblast derived fibronectin.

The t/c33 fragment also shares a common amino terminal sequence with the t/c66 fragment (FIG. 11, line 1), beginning with alanine at position 1583, and it also lacks the EDIII domain. These results illustrate that the amino terminal sequences of these fragments are identical, and support the contention that the size heterogeneity of the 41/c33 and t/c66 heparin binding fragments results from the action of trypsin within the type IIIcs insert of the A chains of plasma fibronectin.

Localization of the 33 kD heparin binding fragment within the A chain of plasma fibronectin was established by determining the amino terminal sequence of the first 21 amino acids of a tryptic 31 kD fragment. This fragment, which is produced during the purification of 33 and 66 kD heparin binding fragments, contains a free sulfhydryl and originates from the carboxyl terminal end of the A chain of plasma fibronectin. See D. E. Smith and L. T. Furcht, *J. Biol. Chem.*, 257, 6318 (1982). Furthermore, the 31 kD fragment also originates from a subset of fibronectin molecules which give rise to the 33 kD heparin binding fragment of fibronectin.

The amino terminal end of the t31 fragment begins at histidine residue 2040, underlined, line 5 of FIG. 11. This is consistent with the known specificities of trypsin, since the residue to the amino terminal side of this histidine is an arginine. This sequence is present in the type IIIcs insert which occurs in a subset of fibronectin molecules. This fragment contains 9 additional amino acids from the type IIIcs insert, skips the last 31 amino acids of this insert (FIG. 11, line 5, parentheses), then continues as a type III homology (FIG. 11, line 6, underlined) until the tyrosine at residue 2062 where the current sequence information ends. These results demonstrate that the t31 fragment contains a portion (the first 89 amino acids) of the maximum possible 120 residue type IIIcs inserted sequence, in agreement with previously established sequence data for this region of plasma fibronectin. The sequence information indicates the maximum possible carboxyl terminal limit of the t/c33 heparin binding fragment at arginine residue 2039, within the type IIIcs insert (FIG. 11, line 5).

Synthesis of Polypeptides

The polypeptides of the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. 2d ed.,.1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next SOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptides is by amino acid analysis. The polypeptides are first hydrolyzed anaerobically for 24 hours at 110° C. in 6M HCl (constant boiling) or in 4N methanesulfonic acid, when cysteine or tzyptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1

Heparin-Binding Assay

The assay for heparin binding utilizes nitrocellulose sheets as substrata to bind peptides or proteins to be tested for heparin binding activity. Peptides I and II or intact fibronectin (fn) were solubilized in 50 mM $(NH_4)_2CO_3$ and diluted to the concentrations indicated in FIGS. 2 and 3. Nitrocellulose sheets which had been presoaked in 50 mM $NH_4CO_3$ were placed in a 96 well dot blot apparatus (Bethesda Research Laboratories, Bethesda, Md.), and 250 $\mu$l of various concentrations of each peptide were aspirated through the wells. Each well was then washed three times with binding buffer (10 mM Tr4Ls-HCI, pH 8.0, 0.15 M NaCl), and the filters were removed and allowed to air dry overnight. The filters were then equilibriated for 5 minutes at room temperature in binding buffer which contained 10 mM $CaCl_2$. $^3$H-heparin was then diluted to a concentration of 50,000 cpm/ml in binding buffer (with $Ca^{++}$), and nitrocellulose sheets were incubated in the presence of this mixture for 2 hours. The filters were then washed four times with binding buffer, and air dried. The individual spots of samples were cut out of the nitrocellulose and bound heparin was quantitated with a liquid scintillation counter.

A. Polypeptides I and II

Figure 2:
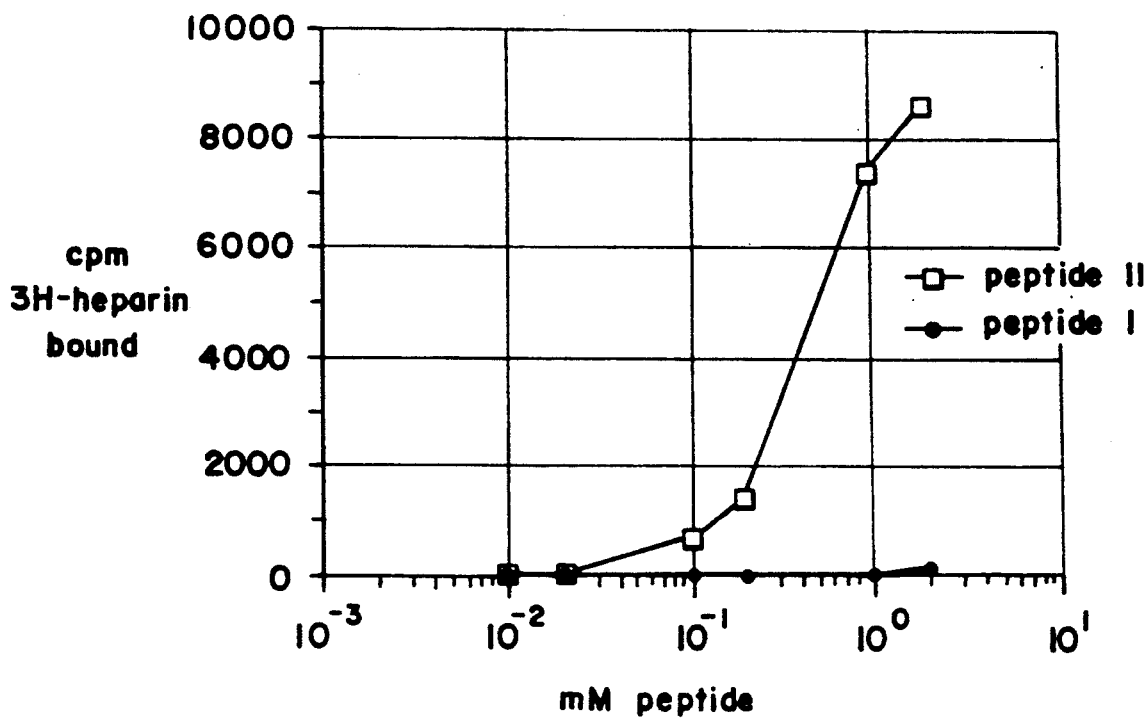
FIG. 2 is a graph depicting the heparin binding activity of peptides I and II of the invention (nitrocellulose binding assay).
Figure 3:
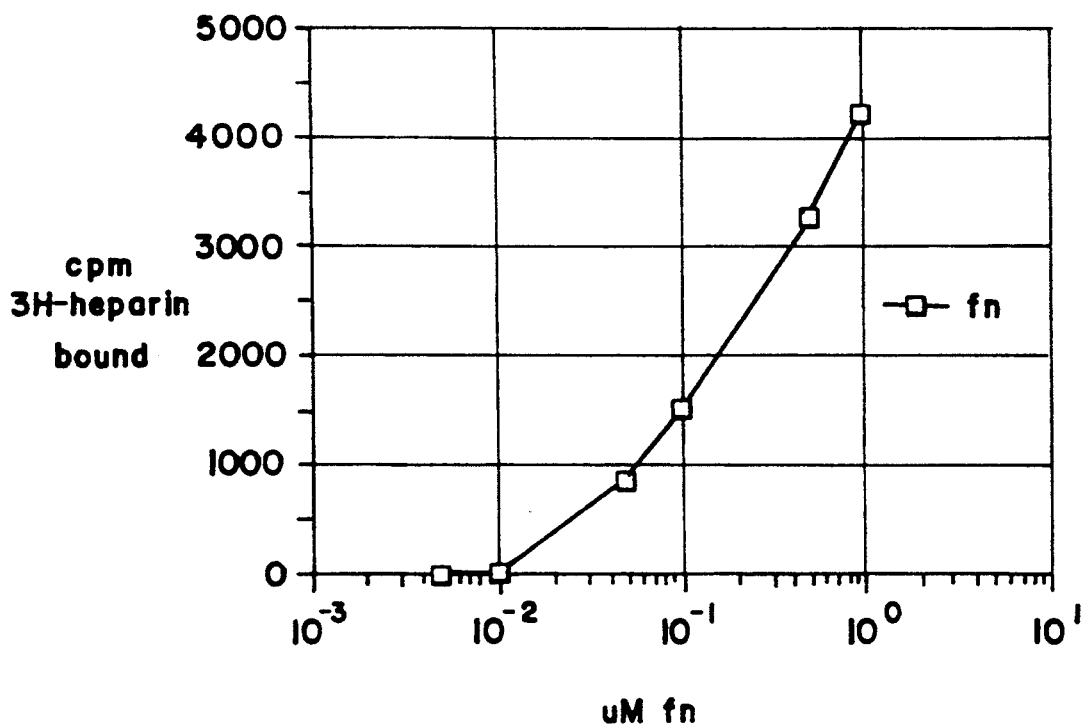
FIG. 3 is a graph depicting the heparin binding activity of fibronectin (fn) (nitrocellulose binding assay).

The results show that peptide II bound $^3$H-heparin in a concentration dependent manner (FIG. 2). In contrast, $^3$H-heparin bound poorly to peptide I at any concentration tested. The lowest concentration of peptide II which promoted $^3$H-heparin binding was $0.25 \times 10^{-4}$M with a saturation of binding observed at higher coating concentrations ($0.25$–$0.5 \times 10^{-2}$M). Similarly, fibronectin also bound $^3$H-heparin in a concentration dependent manner, with maximum binding observed at $10^{-6}$M fibronectin (FIG. 3).

B. Polypeptides IIa and CS I

An additional lysine residue was added at the carboxyl terminus of CS I in order to facilitate coupling of this peptide to the substrata used in this assay.

Both peptides IIa and CS I were then compared for relative heparin-binding activity. Plastic Immulon C plates (Dynayech, Alexandria, Va.) were adsorbed with 100 $\mu$l (in triplicate) of the indicated levels of peptides IIa, CS I or BSA as described. The ability of the 33 kD fragment to bind heparin was also determined, for comparison, although due to the relative size of this fragment compared with the peptides, different coating concentrations were used. The actual coating levels of the 33 kD fragment were 4, 20, 100 and 500 $\mu$g/ml. Following the blocking of nonspecific binding sites with BSA, the ability of these various substrata to bind $^3$H-heparin was determined by the addition of approximately 4,000 disintegrations per minute (dpm) of this ligand. All conditions of the assay were as described in U.S. patent application Ser. No. 89,073, the disclosure of which is incorporated by reference herein.

Figure 4:
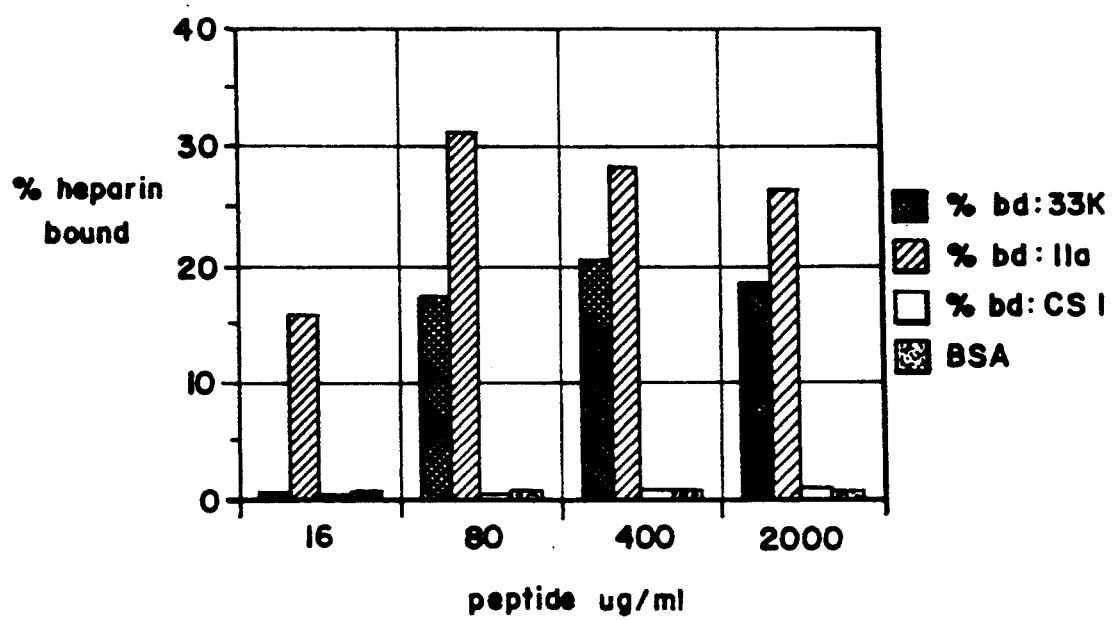
FIG. 4 is a graph depicting the relative heparin-binding activity of peptides IIa and CS I (Immulon C binding assay).

As shown in FIG. 4, peptide IIa retained the ability to bind $^3$H-heparin in a concentration dependent fashion. In contrast, peptide CS I failed to bind heparin at any concentration tested, indicating that the heparin-binding activity ascribed to peptide II does not involve the area of structural overlap with CS I.

C. Polypeptides IIA-A, IIA-B and IIA-C

Figure 5:
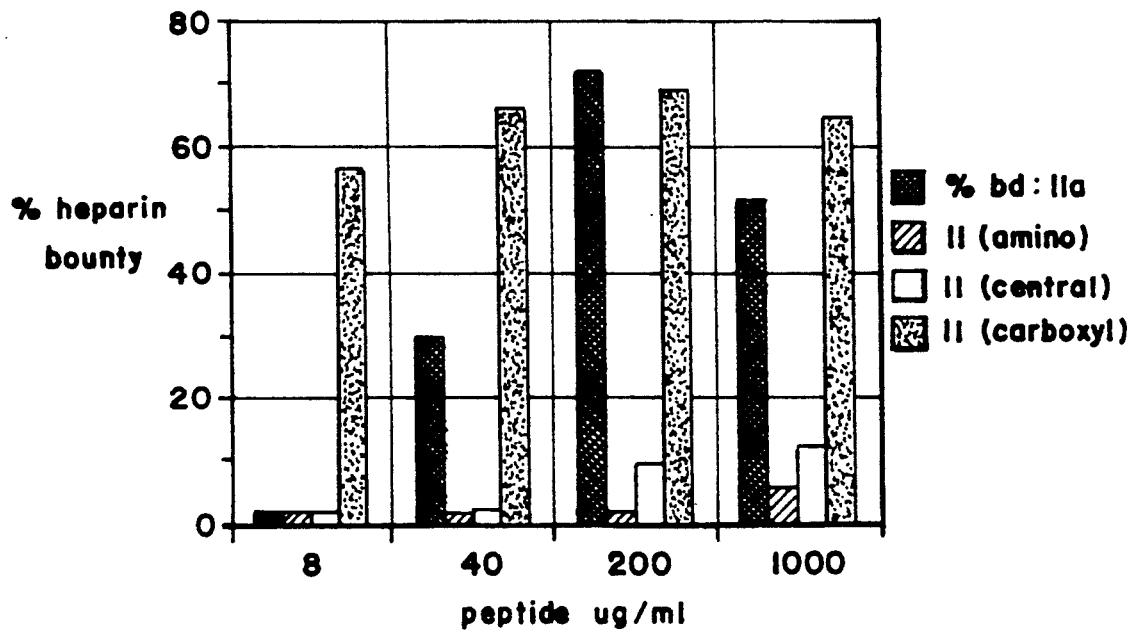
FIG. 5 is a graph depicting the heparin-binding activities of peptides IIA-A, IIA-B, and IIA-C (Immulon C binding assay).

The three peptides derived from peptide IIa and intact peptide IIa, were adsorbed to immulon C plates at the indicated concentrations (100 μl/well) in triplicate and tested for the ability to bind $^3$H-heparin as described hereinabove. The results of this study are summarized on FIG. 5. As demonstrated by these data, peptide IIA-A exhibits extremely poor heparin-binding activity, peptide IIA-B exhibits slightly higher heparin activity at high coating concentrations, whereas peptide IIa-C exhibits extremely high heparin-binding activity, even when used at very low coating concentrations. In fact, peptide IIa-C binds heparin much better than does the parent peptide (peptide IIa), despite the fact that the net charge on peptide IIa-C is (+3) whereas the net charge on peptide IIa is (+4). This demonstrates that net charge per se is not the only primary consideration for the heparin-binding activities observed in synthetic peptides derived from fibronectin. Rather, a specific primary structure is crucial for this activity. In the case of peptide IIa, (KNNQKSEPLIGRKKT) the heparin-binding activity can be localized to the carboxyl terminal third of this peptide (corresponding to the sequence LIGRKKT, peptide IIa-C). Furthermore, at least one of the two lysin residues in this peptide is important for heparin-binding activity, since peptide II(central), which contains an arginine, binds heparin much more weakly than peptide II(carboxyl), which contains the same arginine and two additional lysines.

D. Polypeptides III-V

Figure 6:
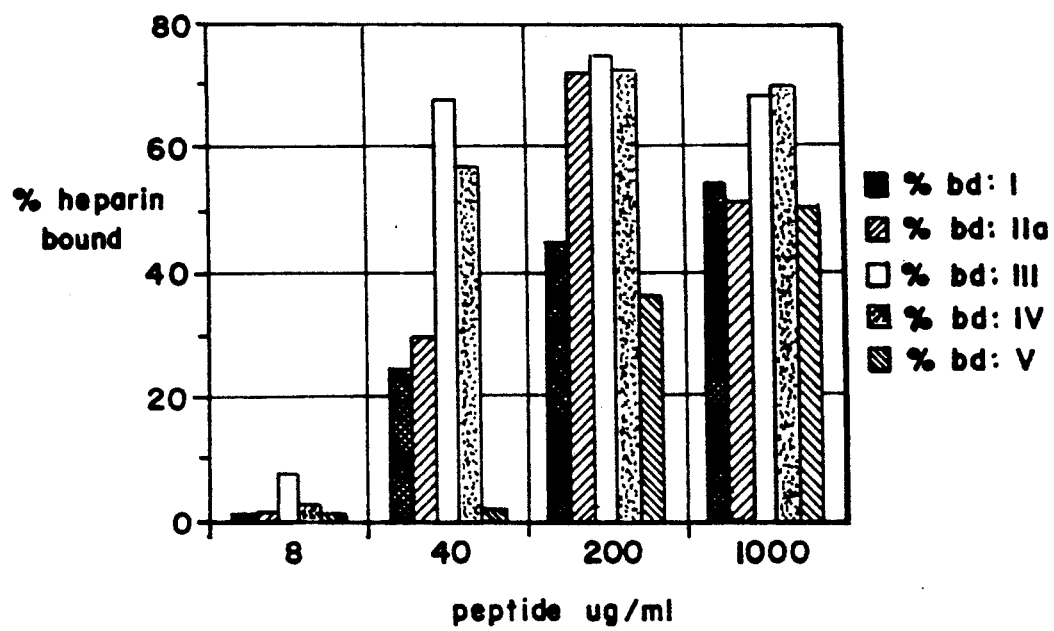
FIG. 6 is a graph depicting the relative heparin-binding activity of peptides I, IIa and III-V (Immulon C binding assay).

Peptides I, IIa and III-V were adsorbed at the indicated concentrations (100 μl/well), in triplicate, to Immulon C plates as described hereinabove. Peptides III-V bind $^3$H-heparin substantially in the solid phase heparin-binding assay, as shown in FIG. 6, and peptides III and IV bind heparin more strongly than does peptide V. Importantly, peptide I, which did not bind heparin well in the nitrocellulose-binding assay, bound heparin well and specifically in the Immulon C binding assay.

The specificity of each peptide for heparin binding is indicated by the fact that the 50% inhibition point $^3$H-heparin binding caused by dextran sulfate or chondroitin/dermatan sulfate is at a concentration which is 1 to 3 orders of magnitude higher than that exhibited by heparin. These results are similar to those observed for intact fibronectin or for peptides I and II.

EXAMPLE 2

Neurite Outgrowth Assay

A. Preparation of Plates

Peptides i, ii, IIa, III, CSI or intact fibronectin were diluted in Voller's buffer (0.05M Carbonate buffer, PH 9.6) and 100 μl of each concentration was dispensed into 96 well tissue culture plates in triplicate. The plates were then placed in a sterile hood overnight to evaporate the buffer and to dry the peptides onto the plate. The following morning, 200 μl of phosphate-buffered saline (PBS) containing 5 mg/ml bovine serum albumin (PBS/BSA) were added to each well and the plates were incubated for an additional 3 hours. At that point, the PBS/BSA was aspirated and cells in the appropriate media were added to each well.

B. Isolation of Neurons and Assay for Neurite Outgrowth

Embryonic CNS nerve cell cultures were prepared by the method of Rogers et al., *Devel. Biol.*, 98, 212–220 (1983). Briefly, spinal cords from 6-day chick embryos were isolated and their dorsal halves removed and placed in Ca$^{++}$-MG$^{++}$ (CMF) Hank's balanced salt solution for 10 minutes at 37° C. Only the ventral portions, containing predominantly motor neurons, were prepared for culture. The cords were then dissociated in 0.25% trypsin (Bactotrypsin, Difco) in CMF Hanks for 25 minutes at 37° C. The trypsin containing medium was replaced with Ham's F12, buffered with HEPES and supplemented with 10% fetal calf serum, and the cells repeatedly pipetted to complete dissociation. The single-cell suspension was pelleted by centrifugation, rinsed with Ham's F12-HEPES plus serum, centrifuged, and resuspended in Ham's F12 supplemented with sodium bicarbonate and glutamine (2 mM), penicillin (100 U/ml), streptomycin (100 U/ml) and plated into wells which had been prepared as described below in the presence and absence of the indicated concentrations of heparin. Cultures were incubated for 24 hours at 37° C. in a humidified incubator in 5% CO$_2$ and then fixed in glutaraldehyde. The number of neurons with neurites was quantitated by randomly sampling 10 fields with the aid of a dissecting microscope.

C. Polypeptides I and II

The results of this assay are summarized on Tables IV and V, below.

TABLE IV

| | Comparision of Neurite Extension by CNS Neurons on Peptide I and Peptide II | |
|---|---|---|
| Coating | Number of Neurons with Neurites | |
| Conc.* | Without Heparin | With 10 μg/ml Heparin |
| I | 12;3** | 3 |
| II | 220;194** | 75 |
| Control (BSA) | 2 | 2 |

*500 μg/ml
**Data represented as duplicate values.

TABLE V

| Dose Response of Peptide II | |
|---|---|
| Coating Concentration of Peptide II | Number of Neurons* with Neurites |
| 2 mg/ml | 39;70 |
| 1 mg/ml | 47;51 |
| 500 μg/ml | 47;32 |
| 250 μg/ml | 16;42 |
| Background | 8;8 |

*Data represented as duplicate values

These results indicate that peptide II is much more effective than peptide I at promoting neurite outgrowths and that the neurite promoting activity of peptide II is apparently related to the heparin-binding activity of this peptide. Thus, peptide II may be useful in providing a synthetic substratum to promote nerve growth in situations where nerve regeneration is desirable (e.g., in crush injuries).

D. Polypeptides IIa and CS I

Further evidence for the distinctive nature of peptides IIa and CS I was obtained by examining the growth of neurites exhibited by central and peripheral system embryonic chicken neurons when plated onto substrata coated with these peptides.

Substrata were coated with 100 μl of a 500 μg/ml solution of the indicated peptides or with 5 μg/ml of the 33 kD heparin-binding fragment of fibronectin as described hereinabove. Following the blocking of nonspecific sites with BSA, suspensions of either central nervous system CCNS) neurons isolated from the spinal cords of emoryonic chickens, or peripheral nervous system (PNS) neurons isolated from the dorsal root ganglia of embryonic chickens, were plated onto the various coated substrata. Data represent the average number of neurons expressing neurites in these culture, and represent the mean of triplicate cultures.

Figure 7:
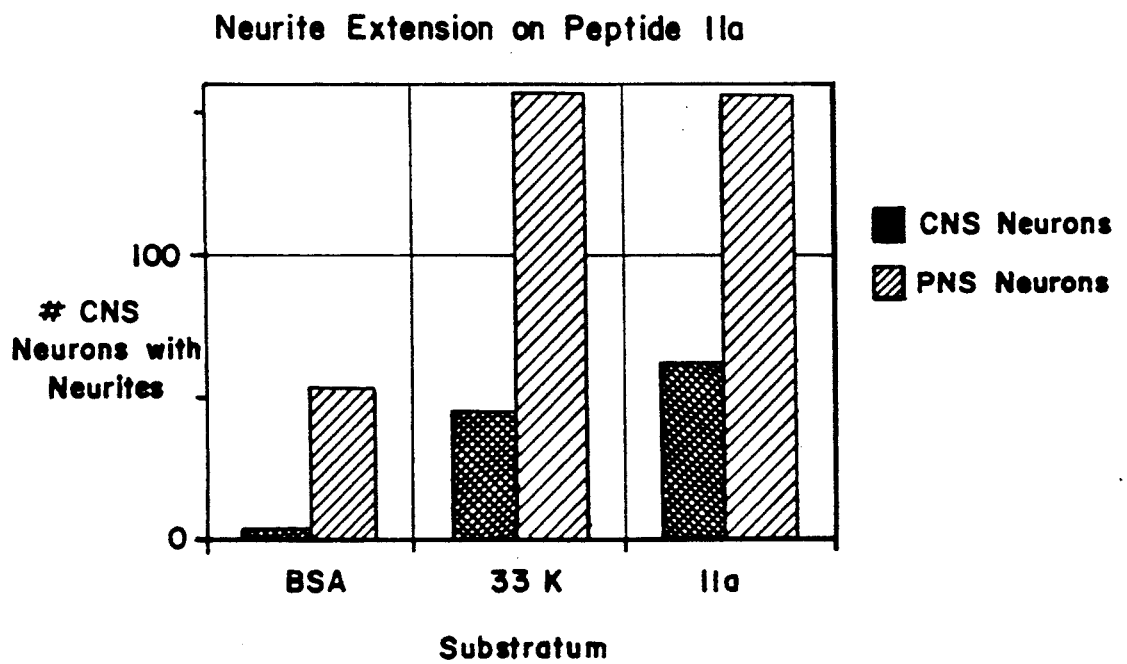
FIG. 7 is a graph depicting the neurite extension promoted by peptide IIa.
Figure 8:
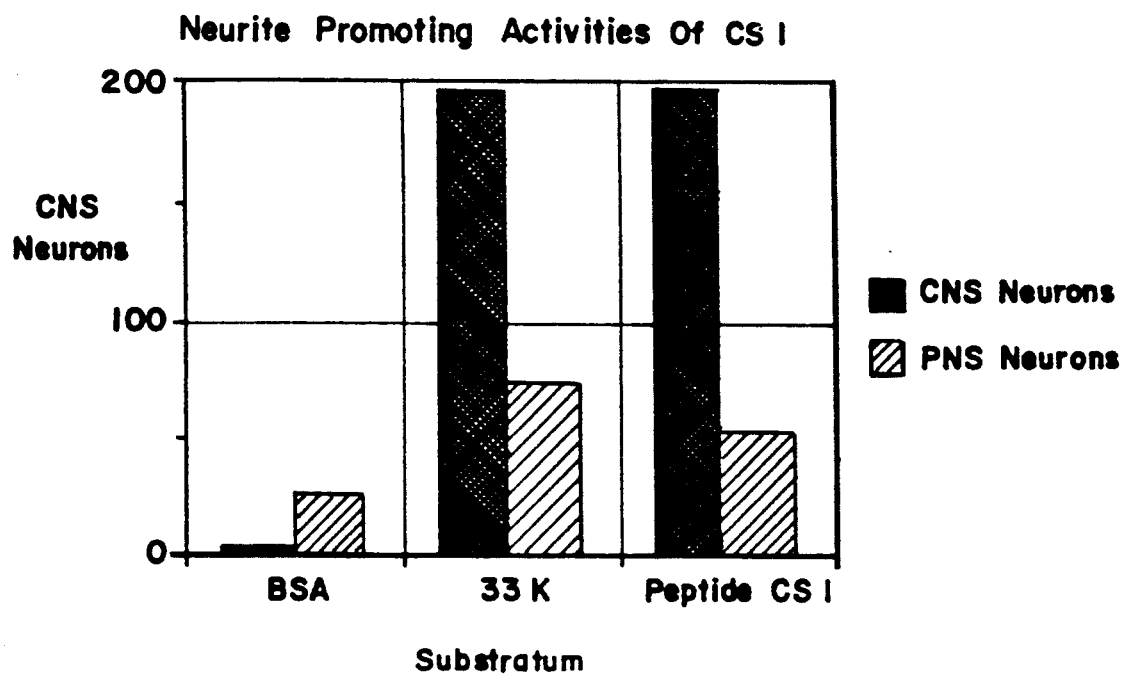
FIG. 8 is a graph depicting the neurite extension promoted by peptide CS I.

As shown in FIGS. 7 and 8, both peptides were able to promote neurite extension by embryonic neurons. However, CNS neurons appeared to be preferably stimulated by peptide CS I, while peptide IIa appeared most effective at stimulating neurite extension by peripheral neurons. Thus, we conclude that, despite the three residue overlap between peptide II and peptide CS I, the biological activity of each peptide is due to distinct and unique structural determinants.

E. Peptide III

Figure 9:
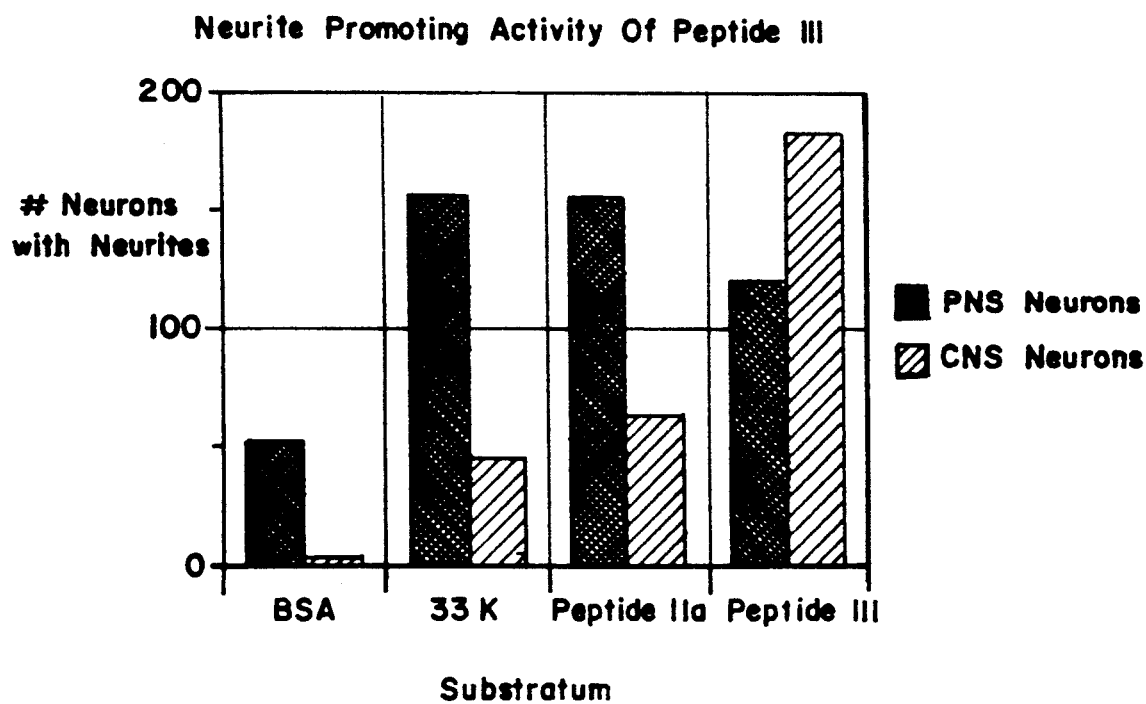
FIG. 9 is a graph depicting the neurite extension promoted by peptide III.

Peptide III was examined for the ability to promote neurite outgrowth by embryonic chicken neurons in vitro. As shown in FIG. 9, peptides IIa and III showed distinct differences in the ability to promote neurite outgrowth PNS and CNS neurons. Both peptides IIa and III demonstrate neurite promoting activity in both populations of neurons, however, peptide III is far more capable of promoting neurite extension by CNS neurons, whereas peptide IIa appears more effective at promoting neurite extension by PNS neurons.

EXAMPLE 3

Adhesion of Endothelial Cells

A Isolation of Bovine Aortic Endothelial Cells

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM Na₂HPO₄, pH 7.2) and processed within 2 hours. Crude collagenase (CLS III, 125-145 units per mg dry weight, Cooper Biomedical) was used at 2 mg/ml in Dulbecco's modified Eagle's medium (DMEM) (GIBCO). The vessel was clammed at the distal end, filled with the collagenase-PBS solution and digestion was carried out for 10 minutes. The lumenal contents were harvested, followed by the addition of fresh collagenase for two additonal 10-minute periods. The enzyme-cell suspensions were added to an equal volume of DMEM containing 10% fetal bovine serum (FBS) to inhibit the enzyme and spun in a centrifuge at 400×g for 10 minutes. The resulting cell pellet was resuspended in DMEM containing 10% FBS, 100 units/ml of penicillin G, 100 μg/mi of streptomycin and 100 μg/ml of crude fibroblast growth factor. Cells are cultured in 75 cm² flasks in a humidified 5% $CO_2$ atmosphere at 37° C. Cultures were fed twice a week with the same medium and cells were used in assays when approximately 75% confluent. Cells were identified as endothelial in nature by characteristic cobblestone morphology, contact inhibition of growth upon reaching confluency, and positive immunofluorescent staining for factor VIII:RAG (Miles Laboratories) [S. Schwartz, In Vitro, 14, 966 (1978)]. Only endothelial cells, mesa aryocytes and platelets are known to contain the factor VIII,RAG. This method routinely gives a high yield of endothelial cells with little contamination (less than 5%) by smooth muscle cells, pericytes or fibroblasts as judged by phase contrast microscopy as well as by immunostaining.

B. Aortic Endothelial Cell Adhesion Assay

Adhesion was measured using 96 well microtiter plates adsorbed with fibronectin or peptides I and II. Cultures of cells which were 60-80% confluent were metabolically labeled overnight with the addition of 10 μCi/ml of ³H•amino acids. On the day of the assay, the cells were harvested by trypsinization, the trypsin was inhibited by the addition of serum, and the cells were washed free of this mixture and resuspended in DMEM buffered with HEPES at PH 7.2. The adhesion medium also contained 5 mg/ml BSA. The cells were adjusted to a concentration of $3-4 \times 10^4$/Ml, and 100 μl of this cell suspension was added to the wells. The assay mixture was then incubated at 37° C. for 90 minutes. At the end of the incubation, the wells were washed with warm PBS containing 10 mM $Ca^{++}$, and the adherent population was solubilized with 0.5N NAOH containing 1% sodium dodecyl sulfate. The solubilized cells were then quantitated using a liquid scintillation counter. Each determination was done in triplicate. The results of this study are summarized in Table VI, below.

TABLE VI

| Coating Concentration | Adherent Cells (Counts Per Minute) |
|---|---|
| Background | 403 |
| Peptide I | |
| 40 μg/ml | 1024 |
| 400 μg/ml | 1107 |
| 4000 μg/ml | 981 |
| Peptide II | |
| 40 μg/ml | 901 |
| 400 μg/ml | 1734 |
| 4000 μg/ml | 14,199 |
| Fibronectin | |
| 5 μg/ml | 13,714 |

These results indicate that peptide II is much more effective than peptide I at promoting endothelial cell adhesion, in agreement with the results observed for neurons. Thus, peptide II may be useful to promote endothelial cell adhesion to artificial or natural substrata.

EXAMPLE 4

Adhesion of Cancer Cells

A. Isolation of Metastatic Melanoma Cells

Highly metastatic melanoma cells, K1735M4, were originally provided by Dr. I. J. Fidler of Houston, Tex. When the cells were received, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments. This precaution is taken to minimize phenotypic drift that can occur as a result of continuous in vitro passage. The cells were cultured-in Dulbecco's Modified Eagle's Medium containing 5% heat inactivated fetal calf serum. The cultures were grown in 37° C. incubators with a humidified atmosphere containing 5% $CO_2$. Cells were subcultured twice weekly by releasing cells gently from the flask, using 0.05% trypsin and 1 mM EDTA.

The melanoma cells were pulsed in the same fashion as the endothelial cells described hereinabove, except that 2 $\mu$Ci/Ml $^3$HTd(tritiated thymidine) was added to each culture instead of amino acids. The labeled cells were harvested as described for the endothelial cells. The cell adhesion assay was identical to that described hereinabove for the bovine aortic endothelial cell assay.

1. Polypeptides I and II

The results of this assay are summarized on Table VII, below.

TABLE VII

| Coating Concentration | Tumor Cell Adhesion* Adherent Cells (Counts Per Minute) |
|---|---|
| Background | 1400 |
| Peptide I | |
| 40 µg/ml | 3900 |
| 200 µg/ml | 3500 |
| 400 µg/ml | 3000 |
| 2000 µg/ml | 4000 |
| Peptide II | |
| 40 µg/ml | 4600 |
| 200 µg/ml | 4700 |
| 400 µg/ml | 4300 |
| 2000 µg/ml | 3900 |
| Fibronectin | |
| 1 µg/ml | 4700 |
| 10 µg/ml | 7900 |
| 50 µg/ml | 11,000 |
| 100 µg/ml | 9700 |

*Measured one hour following the start of the assay.

In contrast to the results obtained above using neurons and endothelial cells, peptides I and II are both capable of promoting the adhesion of melanoma cells. This may suggest cell specific differences in the adhesion of different cell types to this region of fibronectin.

2. Polypeptides II, IIa and CS I

Polypeptides II, IIa and CS I were tested for the ability to promote the adhesion of melanoma cells. A comparison of the melanoma adhesion promoting activities is shown in Table VIII, below.

TABLE VIII

| Melanoma Cell Adhesion to Polypeptides | |
|---|---|
| Concentration (µg/ml) | Percent Adhesion |
| Peptide II(80) | 13.7 |
| Peptide II(400) | 11.3 |
| Peptide IIa(80) | 6.4 |
| Peptide IIa(400) | 18.1 |
| Peptide CS I(80) | 71.7 |
| Peptide CS I(400) | 71.0 |
| Bovine Serum Albumin | 3.5 |

As demonstrated by the data on Table VIII, peptides II, IIa and CS I promoted the adhesion of melanoma cells in culture. Importantly, the deletion of the DEL sequence from peptide II did not eliminate the ability of this peptide to promote cell adhesion. Furthermore, the comparatively high level of melanoma adhesion-promoting activity in CS I indicates that the failure of the peptide to bind $^3$H-heparin was not due to a lack of peptide on the substratum (since identical coating protocols were used for both the cell adhesion and heparin-binding assays).

It is clear that peptides IIa and CS I bind melanoma cells through distinct mechanisms. The heparin-binding activity of IIa strongly suggests that adhesion of melanoma cells to this peptide is related to the heparin-binding properties of the peptide. These results are consistent with an ability of peptide IIa to interact with cell surface proteoglycansglycosaminoglycans on melanoma cells (which have heparin-like qualities). In contrast, peptide CS I apparently promotes adhesion of tumor cells by a heparin independent mechanism. Thus, while melanoma cells adhere to both CS I and peptide IIa, the biological activity of each peptide is distinctive.

3. Peptide III

Peptide III was examined for the ability to promote melanoma cell adhesion and spreading, as described hereinabove.

Figure 10:
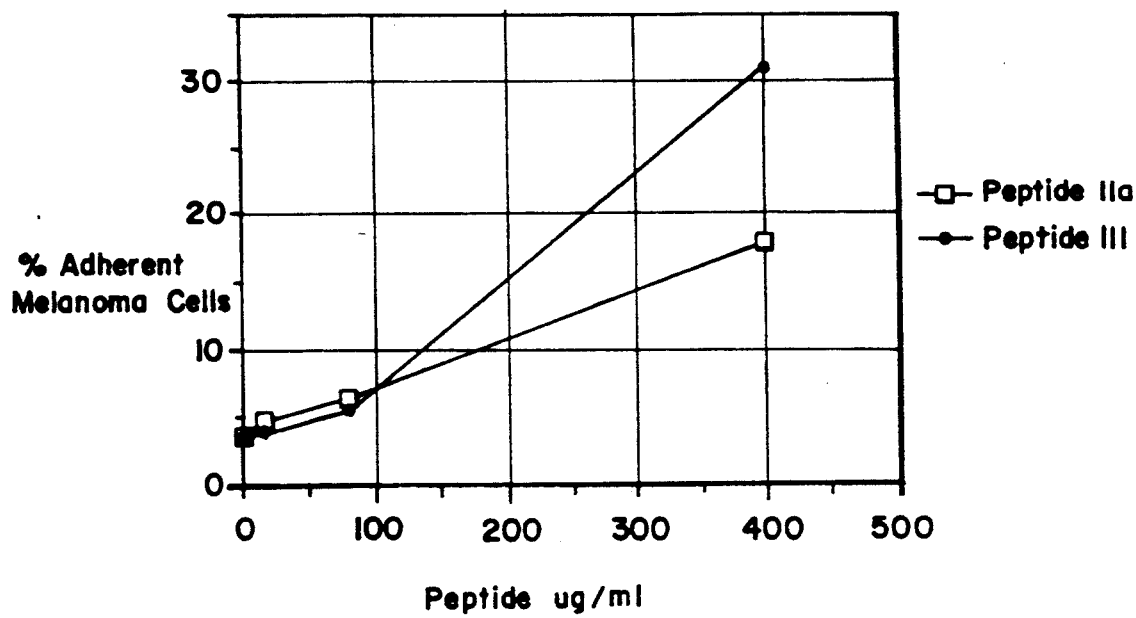
FIG. 10 is a graph depicting the relative melanoma cell adhesion promoted by peptides IIa and III.

As shown in FIG. 10, peptide III is active at promoting melanoma cell adhesion in a concentration dependent fashion. In fact, peptide III is twice as active as peptide IIa at the highest concentration tested, suggesting that it could have a higher affinity than peptide IIa for the surface of melanoma cells. This result is consistent with the greater ability of low concentrations of peptide III to bind $^3$H-heparin when compared to peptide IIa.

A number of practical applications for these polypeptides can be envisioned. Such applications include the promotion of the healing of wounds caused by the placement of natural or synthetic substrata within the body. Such synthetic substrata can include artificial vessels, intraocular contact lenses, hip replacement implants, nerve guides and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type an a particular surface prior to grafting. An example of such an approach is the induction of endothelial cell growth on a prosthetic device such as a blood vessel or vascular graft, which is generally woven or knitted from a synthetic resin such as nitrocellulose, expanded polytetrafluoroethylene or polyester fiber, particularly Dacron TM (polyethylene terephthalate) fiber. Hydrogels such as polymethylolmethacrylamide (PMMA) can also be used for implants in the body or for objects to be used in contact with mucous membranes such as contact lenses. See U.S. Pat. No. 3,966,902.

Devices intended for cardiac insertion include temporary left ventricular assist devices, heart valves, intraortic balloon pumps and artificial hearts. Such devices are preferably formed from synthetic resins such as polyether-type polyurethane elastomers (Cardiothane TM, Kontron) or from vulcanized polyolefin rubbers (Hexsyn TM, Goodyear).

Most types of cells are attracted to fibronectin and to the present polypeptides, but endothelial cells, epithelial cells and fibroblastic cells in particular are attracted to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumas, e.g., spinal cord injuries.

In such cases, it may be advantageous to couple or bind the peptide to a biological molecule, such as collagen, a glycosaminoglycan or a proteoglycan. Collagens, proteoglycans and glycosaminoglycans are major components of connective tissues and basement membranes. In some cases, prosthetic devices formed entirely or in part from naturally-occurring mammalian tissues instead of synthetic polymers are used. One example is the use of porcine heart valves to replace defective human heart valves. Such artificial valves can also comprise human dura matter or bovine pericardium. Another example is the use of bovine arteries as vascular grafts.

It may be useful to coat surfaces of these biological substrata with the present polypeptides, in order to modify the cellular response, in vivo, thus improving the therapeutic outcome. This can be achieved by a variety of methods known to the art, e.g., by direct binding of the polypeptides to the target surfaces based on the affinities described hereinabove, or by the covalently bonding the polypeptides to the substrate using various crosslinking reactions or reagents. For a review of the use of synthetic resins and biomaterials in prosthetic devices, see *Chem. & Eng. News* Apr. 14, 1986) at pages 30–48, the disclosure of which is incorporated by referents herein.

It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include catheters, and controlled drug delivery reservoirs or infusion pumps.

Also, the polypeptides, e.g., I and II, can be used to promote endothelial, fibroblast or epithelial cell adhesion to naturally occurring or artificial substrata intended for use in vitro. For example, a culture substratum such as the wells of a microtiter plate or the medium contacting surface of microporous fibers or beads, can be coated with the cell-attachment polypeptides. This can obviate the use of fibronectin in the medium, thus providing better defined conditions for the culture as well as better reproducibility.

As one example of commercial use of cell-attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of fibronectin in the growth medium and the present polypeptides are expected to provide an improved, chemically-defined coating for such purposes. Other surfaces or materials may be coated to enhance attachment, such as glass, agarose, synthetic resins or long-chain polysaccharides.

The invention has been described with reference to various specific and preferred embodiments and techniques. However, it should be understood that many variations and modifications may be made while remaining within the spirit and scope of the invention.

What is claimed is:

1. A cell culture substrate adapted for in vitro cell culture having a surface coated with a polypeptide of the formula:

lys-asn-asn-gln-lys-ser-glu-pro-leu-ile-gly-arg-lys-lys-thr, leu-ile-gly-arg-lys-lys-thr, tyr-arg-val-arg-val-thr-pro-lys-glu-lys-thr-gly-pro-met-lys-glu, ser-pro-pro-arg-arg-ala-arg-val-thr, trp-gln-pro-pro-arg-ala-arg-ile, or mixtures thereof.

2. The cell culture substrate of claim 1 wherein said surface is made of a synthetic resin.

3. The cell culture substrate of claim 1 wherein said surface constitutes a portion of a bead.

4. The cell culture substrate of claim 1 wherein said surface constitutes a portion of a microporous fiber.

5. The cell culture substrate of claim 1 wherein said surface constitutes the wells of a microtiter plate.

* * * * *